United States Patent [19]

Arretz

[11] Patent Number: 4,891,445
[45] Date of Patent: Jan. 2, 1990

[54] SYNTHESIS OF TERTIARY MERCAPTANS FROM ISOBUTYLENE HOMOPOLYMERS

[75] Inventor: Emmanuel Arretz, Pau, France

[73] Assignee: Societe Nationale Elf Aquitaine (Production), France

[21] Appl. No.: 288,135

[22] Filed: Dec. 22, 1988

[30] Foreign Application Priority Data

Feb. 17, 1987 [FR] France .................... 88 01880

[51] Int. Cl.$^4$ ............................. C07C 148/00
[52] U.S. Cl. ................................. 568/72
[58] Field of Search ......................... 568/72

[56] References Cited

U.S. PATENT DOCUMENTS 4,565,893  1/1986  Arretz et al. ................ 568/72
4,582,939  4/1986  Perozzi et al. .............. 568/72

*Primary Examiner*—Mary E. Ceperley
*Attorney, Agent, or Firm*—Stevens, Davis, Miller & Mosher

[57] ABSTRACT

The invention relates to the synthesis of tertiary mercaptans from isobutylene homopolymers and from hydrogen sulphide by means of heterogeneous catalysis.

In the processs according to the invention, the reaction is carried out at a temperature below 45° C., preferably between 0° and 35° C., in the presence of a catalyst consisting of a dry cation exchange resin.

Excellent yields of tertiary mercaptan are thus obtained, while the formation of undesirable byproducts is virtually avoided.

9 Claims, No Drawings

SYNTHESIS OF TERTIARY MERCAPTANS FROM ISOBUTYLENE HOMOPOLYMERS

FIELD OF THE INVENTION

The present invention relates to mercaptans and manufacture of tertiary mercaptans from isobutylene homopolymers.

BACKGROUND OF THE INVENTION

It is known that the formation of tertiary mercaptans by reaction of hydrogen sulphide with isobutylene homopolymers is generally accompanied by secondary products, more particularly products of decomposition of the isobutylene homopolymer, giving both lower olefins and the corresponding mercaptans. Mention may be made in this respect of U.S. Pat. Nos. 2,101,096; 2,426,646; 2,435,545 and 3,166,498, where the formation of tert-butyl mercaptan is observed for triisobutylene as starting olefin. These patents are hereby incorporated by reference.

The same applies, although in a lesser degree, to the process described in French Pat. No. 2,531,426, which concerns the synthesis of mercaptans in the presence of a catalyst comprising a cation exchange resin. The patent is incorporated by reference. The patent recommends that the temperature be controlled between the strict limits of 45° and 75° C. or, better, between 50° and 70° C. This process gives excellent results and is particularly efficient for the production of tert-butyl mercaptan, of tert-nonyl mercaptan and of tert-dodecyl mercaptan from isobutylene, propylene trimer and propylene tetramer, respectively. However, for isobutylene homopolymers such as, for example, diisobutylene or triisobutylene, a significant formation of light byproducts is also observed. Their presence in the reaction products requires purification by distillation and results in a final loss of active material in relation to the desired output of the tertiary mercaptan.

DETAILED DESCRIPTION OF THE INVENTION

It has now been found that for isobutylene homopolymers much better results are obtained when the reaction is carried out at a temperature below 45° C. Surprising results are obtained more particularly at temperatures as low as 5°–10° C., at which the selectivity for the mercaptan corresponding to the starting homopolymer is practically complete, without the reaction rate or the reactor output rate being significantly affected.

The process according to the invention for the preparation of tertiary mercaptans by reaction of hydrogen sulphide with an isobutylene homopolymer is therefore characterized in that the reaction is carried out at a temperature below 45° C., preferably between 0° and 35° C., in the presence of a catalyst consisting of a dry cation exchange resin.

Although it is possible to operate at any pressure between 1 and 50 bars, it i preferable to work at a pressure ranging from 5 to 16 bars on an industrial scale. The low temperatures used according to the invention are particularly favorable to the dissolution of hydrogen sulphide in isobutylene homopolymers and make it possible to operate at moderate pressures, particularly below 10 bars.

As in the known processes, it is appropriate to use excess hydrogen sulphide. The molar ratios of $H_2S$/isobutylene homopolymer is between 1.2 and 10, and preferably between 1.5 and 5.

The process according to the invention can be applied to isobutylene homopolymers containing up to 20 carbon atoms. It is of very particular interest, however, for the manufacture of mercaptans derived from diisobutylene, triisobutylene and tetraisobutylene.

All the various polymers and copolymers containing acidic functional groups which are known in the art as cation exchangers are suitable as a catalyst to be used according to the invention. In particular, it is possible to use resins based on sulphonated polystyrene which are crosslinked, in particular with divinylbenzene, acrylic or phenylacrylic resins containing free carboxylic groups, resins of the phenolformaldehyde type derived from phenolsulphonic acids, lignosulphonic exchangers, and the like. Resins of this kind can be found on the market under various names, in particular ALLASSION, CECACIT, WOFATITES, LEVATITES, IMAC, IONAC, AMBERLITES, LIQUOREX, ZEOREX, ZEOCARB, DOWEX, and so on. Sulphonated copolymers of styrene with divinylbenzene are very particularly suitable, for example those found on the market under the names AMBERLYST, LEWATIT or DOWEX. Furthermore, tetrafluoroethylene copolymers with a perfluorosulphonic acid (in particular perfluoro-3,6-dioxa-4-methyl-7-octenesulphonic acid) known under the trademark NAFION may be advantageously used. Whatever the resin is used as a catalyst, care should be taken that it does not contain more than 0.5% of water capable of being determined after drying for 6 hours at 80° C. It is preferably as dry as possible (advantageously less than 0.2% of water).

The process according to the invention may be carried out noncontinuously or continuously according to any known method. Nevertheless, it is preferable to operate continuously, in a stirred reactor or in a tubular reactor packed with catalyst and fed continuously with hydrogen sulphide and isobutylene homopolymer. In certain cases it may be advantageous to recycle the unconverted homopolymer to the reactor.

EXAMPLES

The following examples illustrate the invention without limiting it.

EXAMPLE 1: SYNTHESIS OF TERT-OCTYL MERCAPTAN (a) According to the prior art 200 ml of dry sulphonated Amberlyst 15 resin are placed in a tubular reactor with a capacity of approximately 420 ml (length: 135 cm; bore: 20 mm). Liquid diisobutylene at a rate of 112 g/h (that is 1 mole/h) and 136 g/h of gaseous $H_2S$ (that is 4 moles of $H_2S$ per 1 of diisobutylene) are introduced continuously at the head of the reactor at a pressure of 10 bars. The reactants are mixed intimately before their entry into the reactor, where the reaction mixture is maintained at the temperature of 45° C. The liquid flowing continuously from the reactor is collected and the remaining hydrogen sulphide is degassed. Analyses are carried out both on the crude liquid reaction products and on the gaseous effluents from the reaction, with the aim of establishing the complete balance of the reaction.

Because the formation of byproducts is considerable (approximately 15%), a second test is carried out at the same temperature of 45° C., but this time by operating with reactant flow rates which are 4 times greater, with the intention of improving the selectivity for tert-octyl mercaptan by reducing the contact time of the materials with the catalyst. Virtually no difference is obtained in relation to the first test.

The results of both these tests are shown in the following table:

| DIB (mole/h) | DIB CONVERSION | TOM YIELD | TBM YIELD | OTHER BY-PRODUCTS |
|---|---|---|---|---|
| 1 | 98 | 81.2 | 4.2 | 11 |
| 4 | 97.8 | 80.9 | 3.5 | 12 |

DIB: diisobutylene
TOM: tert-octyl mercaptan
TBM: tert-butyl mercaptan (b) According to the invention Four operations at temperatures below 45° C., namely 5°, 10°, 20° and 30° C., are carried out by operating as previously with a diisobutylene flow rate of 448 g/h and an $H_2S$ flow rate of 544 g/h.

| TEMPERATURE (°C.) | DIB CONVERSION | TOM YIELD | TBM YIELD | OTHER BY-PRODUCTS |
|---|---|---|---|---|
| 30 | 97.6 | 91 | 0.2 | 5 |
| 20 | 97.3 | 92.5 | 0 | 4 |
| 10 | 97.1 | 93 | 0 | 3.6 |
| 5 | 96.5 | 94.2 | 0 | 2.5 |

It is found that, at these temperatures, the yield of desired tert-octyl mercaptan is markedly improved, the formation of tert-butyl mercaptan is virtually eliminated and that of other byproducts is very markedly diminished, while a degree of conversion of diisobutylene of the same order as at 45° C. is maintained.

EXAMPLE 2: SYNTHESIS OF TERT-DODECYL MERCAPTAN

A series of tests is carried out in the same reactor as in Example 1, packed with 200 ml of Amberlyst 15 resin, by introducing continuously at a pressure of 10 bars a mixture comprising liquid triisobutylene at a rate of 121 g/h (that is 0.72 mole/h) and of $H_2S$ at a rate of 122.4 g/h (that is 3.6 moles/h). The reaction temperature is varied for each test in a range of between 45° C. and 10° C. The following table collates the weight compositions of the products identified by analysis in the various reaction effluents.

| TEMPERATURE (°C.) | TIB (%) | TDM (%) | TOM (%) | TBM (%) |
|---|---|---|---|---|
| 45 | 43.6 | 20.4 | 18.1 | 8.2 |
| 30 | 49.6 | 30.5 | 9.1 | 3.0 |
| 20 | 50.4 | 41.3 | 0.8 | 0.15 |
| 10 | 50.7 | 49.2 | 0.1 | 0.05 |

TIB: triisobutylene
TDM: tert-dodecyl mercaptan
TOM: tert-octyl mercaptan
TBM: tert-butyl mercaptan Based on the TIB actually consumed, the yield of TDM at 10° and 20° C. is about 85%. Because the formation of TOM and of TBM at these temperatures is very low, the output can be improved by recycling the unconsumed TIB, without detriment to the quality of the TDM desired.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

I claim:

1. A process for the preparation of tertiary mercaptans from isobutylene homopolymers and from hydrogen sulphide by means of heterogeneous catalystis comprising a reaction carried out at a temperature below 45° C. in the presence of a catalyst comprising a dry cation exchange resin.

2. The process according to claim 1, wherein the reaction temperature is between 0° and 35° C.

3. The process according to claim 1, wherein the cation exchange resin is a sulphonated styrene-divinylbenzene copolymer or a tetrafluoroethylene-perfluorosulphonic acid copolymer.

4. The process according to claim 1, wherein the reaction occurs at a pressure between 1 and 50 bars.

5. The process according to claim 4, wherein the reaction occurs at a pressure between 5 and 16 bars.

6. The process according to claim 1, wherein the molar ratio of $H_2S$/isobutylene homopolymer is between 1.2 and 10.

7. The process according to claim 6, wherein the molar ratio $H_2S$/isobutylene homopolymer is between 1.5 and 5.

8. The process according to claim 1, wherein the isobutylene homopolymer is diisobutylene, triisobutylene or tetraisobutylene.

9. The process according to claim 1, wherein the unconverted isobutylene homopolymer is recycled.

* * * * *